United States Patent
Trogolo et al.

(10) Patent No.: US 6,296,863 B1
(45) Date of Patent: Oct. 2, 2001

(54) ANTIMICROBIAL FABRIC AND MEDICAL GRAFT OF THE FABRIC

(75) Inventors: Jeffrey A. Trogolo, Boston, MA (US); John E. Barry, Derry, NH (US); Steven Holley, Brighton, MA (US)

(73) Assignee: Agion Technologies, LLC, Wakefield, MA (US)

( * ) Notice: Subject to any disclaimer, the term of this patent is extended or adjusted under 35 U.S.C. 154(b) by 0 days.

(21) Appl. No.: 09/197,809

(22) Filed: Nov. 23, 1998

(51) Int. Cl.[7] .............................. A01N 25/34; A61K 9/00; A61L 15/00; A61L 17/00; A61F 2/04; A61F 2/06
(52) U.S. Cl. ......................... 424/404; 424/400; 424/402; 427/2.1; 623/1; 623/12
(58) Field of Search .................................... 424/400, 402, 424/404; 623/1, 12; 427/2, 2.1

(56) References Cited

U.S. PATENT DOCUMENTS

| | | | |
|---|---|---|---|
| 4,525,410 | 6/1985 | Hagiwara et al. | 428/198 |
| 4,525,510 | 6/1985 | Hagiwara et al. | . |
| 4,775,585 | 10/1988 | Hagiwara et al. | 428/323 |
| 4,906,464 | 3/1990 | Yamamoto et al. | 424/78 |
| 4,911,898 | 3/1990 | Hagiwara et al. | 423/118 |
| 4,911,899 | 3/1990 | Hagiwara et al. | 423/118 |
| 4,923,450 | 5/1990 | Maeda et al. | 604/265 |
| 4,938,955 | 7/1990 | Niira et al. | 424/79 |
| 4,938,958 | 7/1990 | Niira et al. | 424/79 |
| 5,003,638 | 4/1991 | Miyake et al. | . |
| 5,009,898 | 4/1991 | Sakuma et al. | 424/618 |
| 5,019,096 | 5/1991 | Fox, Jr. et al. | 623/1 |
| 5,100,671 | 3/1992 | Maeda et al. | 424/443 |
| 5,102,401 | 4/1992 | Lambert et al. | 604/264 |
| 5,157,005 | 10/1992 | Suppiah | 502/62 |
| 5,180,585 | 1/1993 | Jacobson et al. | 424/405 |
| 5,207,706 * | 5/1993 | Menaker et al. | 623/1 |
| 5,244,667 | 9/1993 | Hagiwara et al. | 424/409 |
| 5,296,238 | 3/1994 | Sugiura et al. | 424/604 |
| 5,305,827 | 4/1994 | Steele et al. | 165/133 |
| 5,405,644 | 4/1995 | Ohsumi et al. | 427/2.31 |
| 5,441,717 | 8/1995 | Ohsumi et al. | 423/306 |
| 5,474,797 | 12/1995 | Sioshansi et al. | 427/2.24 |
| 5,492,763 | 2/1996 | Barry et al. | 428/457 |
| 5,509,899 | 4/1996 | Fan et al. | 604/96 |
| 5,520,664 | 5/1996 | Bricault, Jr. et al. | 604/265 |
| 5,556,699 | 9/1996 | Niira et al. | 428/323 |
| 5,562,872 | 10/1996 | Watanabe | 264/145 |
| 5,607,464 | 3/1997 | Trescony et al. | 623/1 |
| 5,697,203 | 12/1997 | Niwa | 53/510 |
| 5,714,430 | 2/1998 | Gehrer et al. | 502/347 |
| 5,714,445 | 2/1998 | Trinh et al. | 510/103 |
| 5,723,110 | 3/1998 | Yamamoto et al. | 424/65 |
| 5,753,251 | 5/1998 | Burrell et al. | 424/426 |
| 5,770,255 | 6/1998 | Burrell et al. | 427/2.1 |

FOREIGN PATENT DOCUMENTS

| | | |
|---|---|---|
| 0 116 865 | 8/1984 | (EP) . |
| 05154174 | 6/1993 | (JP) . |

* cited by examiner

*Primary Examiner*—Shelley A. Dodson
(74) *Attorney, Agent, or Firm*—Steven J. Hultquist; Edward K. Welch, II

(57) ABSTRACT

A medical graft, such as a vascular graft, made of a fabric containing an inorganic antimicrobial agent. The fabric has a coating material with the inorganic antimicrobial agent bonded to it, the agent preferably being a zeolite. The fabric can be porous so as to permit tissue to grow on it with the fabric pores providing attachment sites for the tissue. Alternatively, the fabric can be coated with a tissue biocompatible material, such as collagen. A porous fabric applicable for the graft, and for other medical uses, and a method of manufacturing the porous fabric having a coating thereon to which is bonded an antimicrobial agent, such as a zeolite, also is provided. The fabric is antimicrobial, remains pliable, and is also porous.

29 Claims, 2 Drawing Sheets

FIG. 4
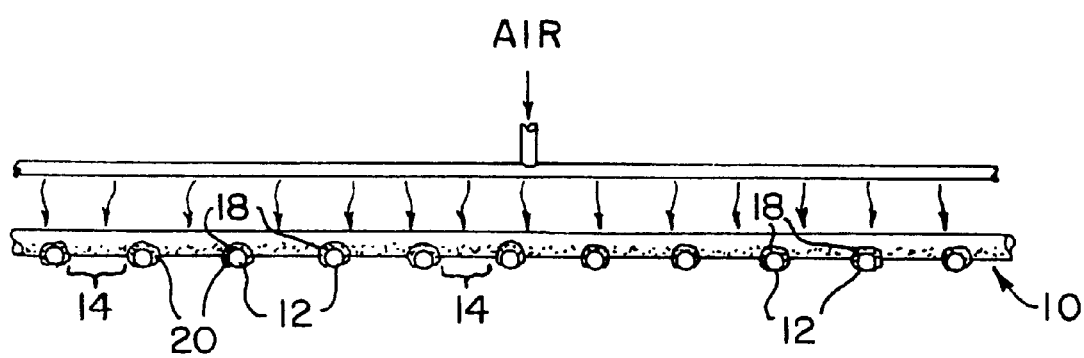
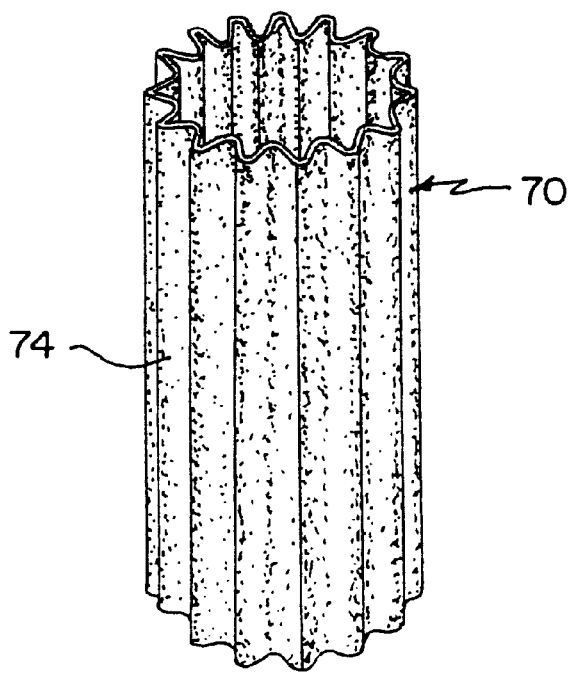
FIG. 5

ANTIMICROBIAL FABRIC AND MEDICAL GRAFT OF THE FABRIC

FIELD OF THE INVENTION

The present invention relates to a fabric having antimicrobial properties and a medical graft, such as a vascular graft, made of such fabric.

BACKGROUND OF THE INVENTION

Various types of grafts are used in the human body for surgical replacement and repair. A graft is a tubular type member typically used to provide a passage for fluid flow between two parts of a vein or artery that has been severed or as a bypass for diseased or deteriorated tissue. For example, grafts are often used in vascular bypass applications, such as for an abdominal aortic aneurism. The graft can either be of natural material, taken from another part of the body of a human or an animal, or it can be of synthetic material. Where the graft is of synthetic material, it would be desirable for it to be able to inhibit the growth of bacteria in the fluid flowing in the graft or from other body parts that come into contact with the graft. Other medical products, such as pledgets and patches, would also desirably have the same properties.

BRIEF DESCRIPTION OF THE INVENTION

The present invention is directed to a graft for medical use that is made of a fabric constraining an inorganic antimicrobial agent. The fabric has the inorganic antimicrobial agent bonded to it, the agent preferably being a zeolite. In the vascular graft application, the fabric fibers are preferably of Teflon or polyester. The fabric can be porous so as to permit tissue to grow on it with the fabric pores providing attachment sites for the tissue. Alternatively, a non-porous fabric is coated with a tissue biocompatible material, such as collagen, which also can be coated on a porous fabric.

The present invention also is directed to an antimicrobial fabric applicable for the graft, and for other medical uses, having a coating thereon to which is bonded an antimicrobial agent, such as a zeolite. When the fabric is porous, it remains pliable and flexible. This type of fabric, which is pliable, has use for other types of medical products such as pledgets and patches.

In a preferred method of manufacturing the porous fabric, the fabric is held under tension in one direction and a mixture of an adherent type coating material, such as a hydrophilic polymer or silicone, is applied which covers the fabric fibers and fills the spaces between the fibers. With the fabric held in tension in both directions, a dusting of the antimicrobial agent is applied onto the coating material while it is still wet. This bonds the agent to the coating material. The fabric is then cured with a pressurized gas, such as air, to dry it. The air under pressure removes all of the matter, coating material and antimicrobial agent, from between the fibers making it porous allowing it to be pliable. In another embodiment, the antimicrobial agent is mixed with the coating material, the mixture is applied to the fabric and the matter between the pores is removed by the pressurized air drying.

If the step of pressurized air drying is omitted, the fabric will dry with the coating material and antimicrobial agent present in the pores as well as with the antimicrobial agent bonded to the fabric fibers. Here, since the fabric does not have pores for tissue attachment sites it is preferred that the fabric be coated with a tissue growth promoting material, such as collagen.

The antimicrobial agent is on the surface of the fabric bonded to the coating material and is available to provide antimicrobial action relative to fluids and body parts that come into contact with it.

OBJECTS OF THE INVENTION

An object of the invention is to provide a medical graft of a fabric containing an inorganic antimicrobial agent.

Another object is to provide a medical graft of a fabric containing an inorganic antimicrobial agent that is coated with a tissue compatible material.

A further object is to provide a porous and pliable antimicrobial fabric useful for medical applications and a method of manufacturing the same.

Still another object is to provide a porous, pliable antimicrobial fabric useful for a medical graft.

Yet a further object is to provide a vascular graft utilizing a porous fabric having antimicrobial properties.

BRIEF DESCRIPTION OF THE DRAWINGS

Other objects and advantages of the present invention will become more apparent upon reference to the following specification and annexed drawings in which:

FIG. 4 is a cross-sectional view of the finished fabric after drying;

FIG. 5 is a view of a vascular graft using the fabric of the invention.

DETAILED DESCRIPTION OF THE INVENTION

All patents, patent applications, and publications listed herein are hereby incorporated by reference in their entireties.

FIG. 5 illustrates a vascular graft 70 made with the inorganic antimicrobial fabric. While the graft illustrated is of the pleated type, such as shown in U.S. Pat. No. 5,607,464, it can be of the more conventional type that has no pleats. The graft 70 is of the generally overall cylindrical construction so that it can be attached between the ends of the body tissue to be connected or used as a bypass. The antimicrobial fabric 72 forming the graft is of one of the types described below.

The outer surface of the graft of FIG. 5 is shown as being coated with a tissue compatible material 74 which can promote tissue growth, such as collagen. The collagen coating is usually used where the fabric is completely coated with the antimicrobial agent. If the graft fabric is porous, it normally is left uncoated since the presence of pores in the fabric provides sites for tissue attachment. However, a porous fabric also can be coated with collagen.

Various types of antimicrobial fabrics useful for the graft 70 are described.

1. Coated Fabric that is Porous

Figure 1:
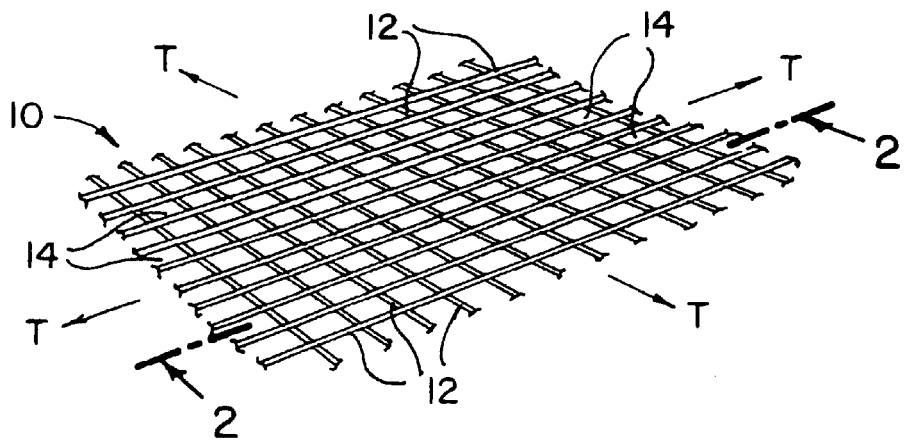
FIG. 1 is a perspective view of a base fabric.

FIGS. 1–4 describe a porous antimicrobial fabric and method of manufacture useful for the graft and which also has other medical uses due to its pliability. In FIG. 1, there a base material comprising a piece of fabric 10 of the mesh type formed by fibers 12 which are laid transverse to each other and which define spaces, or pores, 14 between the fibers. The fibers can be of any suitable material, for example, cotton, nylon polyester, Teflon, e-PTFE and blends of these materials. For the graft application, Teflon or polyester is preferred. The fabric can be either of the woven or non-woven type. The fabric 10 is shown by the arrows T as being able to be held under tension in both directions generally along the fabric length and width, in the directions of the cross-laid fibers, by any suitable mechanism (not shown), for example, rollers, clamps, etc.

Figure 2:
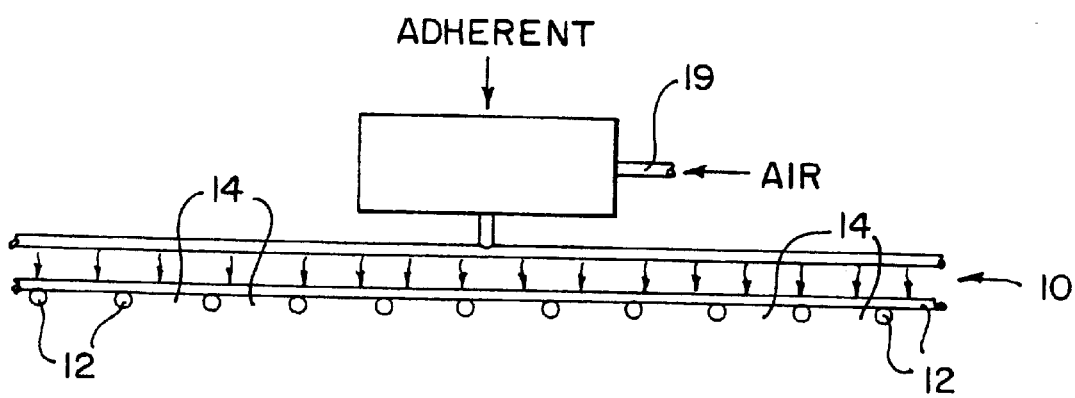
FIG. 2 is a cross-sectional view along lines 2—2 of FIG. 1 showing application of the coating material to the fabric.

FIG. 2 shows the fabric piece 10 in the stage of having an coating of an adherent material 18 applied to one surface. It should be understood that the invention is applicable to performing the process on both fabric surfaces and on the sides of the fabric fibers forming the pores 14. The adherent coating material 18 is a biologically compatible material such as, for example, acrylic, polyurethane, silicone, latex, polyglycolic lactic acid or other biodegradable polymer, especially one that is a hydrophilic, a non-degrading polymer such as a hydrophilic polyurethane, for example TECOPHILIC which is made by Thermedics. These materials all have elastomeric properties.

In a preferred embodiment of the invention, the fabric coating material 18 is applied as a mixture of a high strength RTV dispersed in a solvent, such as xylene. A preferred composition of the mixture is 50% RTV and 50% xylene although the ratio of the two materials can be varied. Increasing the proportion of the coating material in the mixture makes the final fabric product less pliable.

In a preferred manner of application of the coating material, the fabric 10 is held under tension in its lengthwise dimension. The coating material mixture 18 is supplied by a peristaltic pump to an ultrasonic disperser. The ultrasonic disperser creates a fine mist of the mixture that is blown out of the disperser by an air source, illustratively shown by reference numeral 19, to coat the fabric 10. There can be one or more dispersers and air sources on both sides of the fabric and at varying angles to fully coat the entire surfaces of the fabric fibers. Alternatively, only one surface is coated, the two surfaces are coated sequentially, or both surfaces coated at the same time. In the application for the vascular graft, the fabric preferably is coated on both surfaces.

Figure 3:
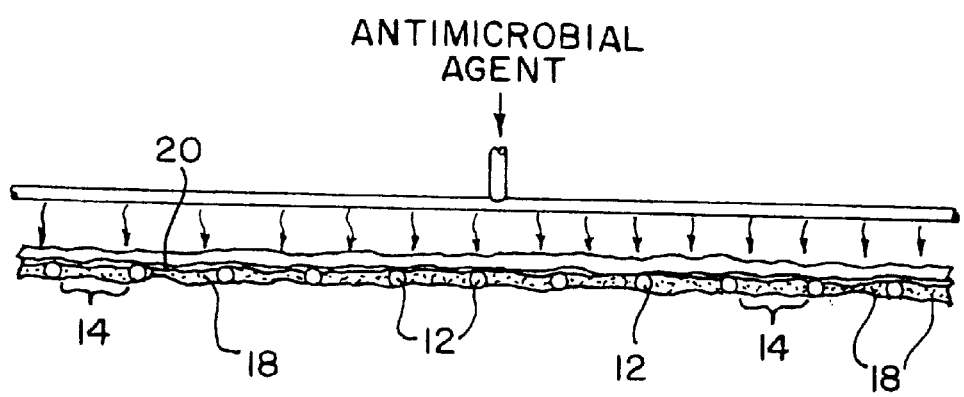
FIG. 3 is a cross-sectional view of the fabric after the antimicrobial agent has been applied.

FIG. 3 shows the fabric 10 having been coated on one side with the coating material 18. As seen, the coating material 18 extends into the openings 14 between the fibers of the fabric and also coats the top of each of the fibers. There is a continuous layer of the coating material 18 over the entire surface of the fabric at this stage of the process. The fabric can be cycled relative to the disperser as many times as needed. That is, the deposition of the coating material mixture on the fabric can be accomplished by applying a desired number of layers to achieve a desired thickness. The layers are contiguous to and mixed with each other. The depth of the coating material 18 on top of the fabric is selected to be between 0.01 and 50 microns, more preferably between 0.1 and 25 microns, and most preferably between 0.1 and 10 microns.

As is also shown in FIG. 3, an inorganic antimicrobial agent 20 in powdered form is applied to the coating material 18 while it is still wet. During this step the fabric preferably is held under tension in both directions, that is, generally along both the fabric length and width. The powdered antimicrobial agent 20 becomes immersed into and bonds with the coating material layer 18 on the fabric.

As to the inorganic antimicrobial agent 20, a number of metal ions, which are inorganic materials, have been shown to possess antibiotic activity, including silver, copper, zinc, mercury, tin, lead, bismuth, cadmium, chromium and thallium ions. These antibiotic metal ions are believed to exert their effects by disrupting respiration and electron transport systems upon absorption into bacterial or fungal cells. Antimicrobial metal ions of silver, gold, copper and zinc, in particular, are considered safe even for in vivo use. Antimicrobial silver ions are particularly useful for in vivo use due to the fact that they are not substantially absorbed into the body. That is, if such materials are used for the antimicrobial fabric, they should pose no hazard to the body.

Antibiotic zeolites also are suitable as the agent. These have been prepared by replacing all or part of the ion-exchangeable ions in zeolite with ammonium ions and antibiotic metal ions, as described in U.S. Pat. Nos. 4,938, 958 and 4,911,898. Such zeolites have been incorporated in antibiotic resins (as shown in U.S. Pat. Nos. 4,938,955 and 4,906,464) and polymer articles (U.S. Pat. No. 4,775,585). Polymers including the antibiotic zeolites have been used to make refrigerators, dish washers, rice cookers, plastic film, chopping boards, vacuum bottles, plastic pails, and garbage containers. Other materials in which antibiotic zeolites have been incorporated include flooring, wall paper, cloth, paint, napkins, plastic automobile parts, catheters, bicycles, pens, toys, sand, and concrete. Examples of such uses are described in U.S. Pat. Nos. 5,714,445; 5,697,203; 5,562, 872; 5,180,585; 5,714,430; and 5,102,401. These applications involve slow release of antibiotic silver from the zeolite particles which is suitable for the antimicrobial fabric.

Antibiotic zeolites are well-known and can be prepared for use in the present invention using known methods. These include the antibiotic zeolites disclosed, for example, in U.S. Pat. Nos. 4,938,958 and 4,911,898.

In one embodiment of the invention, the inorganic antibiotic metal containing composition is an antibiotic metal salt. Such salts include Such salts include silver iodate, silver iodide, silver nitrate, and silver oxide.

Silver nitrate is preferred. These salts are particularly quick acting, as no release from ceramic particles is necessary to function antimicrobially.

Antibiotic ceramic particles useful with the present invention include zeolites, hydroxyapatite, zirconium phosphates or other ion-exchange ceramics. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717; and 5,405,644.

Either natural zeolites or synthetic zeolites can be used to make the antibiotic zeolites used in the present invention. "Zeolite" is an aluminosilicate having a three dimensional skeletal structure that is represented by the formula: $XM_2/nO—Al_2O_3—YSiO_2—ZH_2O$. M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows:

A-type zeolite=7 meq/g; X-type zeolite=6.4 meq/g; Y-type zeolite=5 meq/g; T-type zeolite=3.4 meq/g; sodalite=

11.5 meq/g; mordenite=2.6 meq/g; analcite=5 meq/g; clinoptilolite=2.6 meq/g; chabazite=5 meq/g; and erionite= 3.8 meq/g. These ion-exchange capacities are sufficient for the zeolites to undergo ion-exchange with ammonium and antibiotic metal ions.

The specific surface area of preferred zeolite particles is preferably at least 150 m$^2$/g (anhydrous zeolite as standard) and the SiO$_2$/Al2O$_3$ mol ratio in the zeolite composition is preferably less than 14, more preferably less than 11.

The antibiotic metal ions used in the antibiotic zeolites should be retained on the zeolite particles through an ion-exchange reaction. Antibiotic metal ions which are adsorbed or attached without an ion-exchange reaction exhibit a decreased bacteriocidal effect and their antibiotic effect is not long-lasting. Nevertheless, it is advantageous for imparting quick antimicrobial action to maintain a sufficient amount of surface adsorbed metal ion.

During the ion exchange process, if the concentration of metal ions in the vicinity of the zeolite surface is high, there is a tendency for the antimicrobial metal ions (cations) to be converted into their oxides, hydroxides, basic salts, etc., which deposit in the micro pores or on the surfaces of the zeolite. This deposition may adversely affect the bactericidal properties of the ion-exchanged zeolite.

In an embodiment of the antibiotic zeolites, a relatively low degree of ion exchange is employed to obtain superior bactericidal properties. It is believed to be required that at least a portion of the zeolite particles retain metal ions having bactericidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration as compared with solutions conventionally used for ion exchange.

The antibiotic metal ion is preferably present in the range of from about 0.1 to 20 wt. % of the zeolite. In one embodiment, the zeolite contain from 0.1 to 20 wt. % of silver ions and from 0.1 to 20 wt. % of copper or zinc ions. Although ammonium ion can be contained in the zeolite at a concentration of about 20 wt. % or less of the zeolite, it is desirable to limit the content of ammonium ions to from 0.5 to 15 wt. %, preferably 1.5 to 5 wt. %. Weight % described herein is determined for materials dried at temperatures such as 110° C., 250° C. or 550° C. as this is the temperature employed for the preferred post-manufacturing drying process.

A preferred antibiotic zeolite is type A zeolite containing either a combination of ion-exchanged silver, zinc, and ammonium or silver and ammonium. One such zeolite is manufactured by Shinegawa, Inc. under the product number AW-10N and consists of 0.6% by weight of silver ion-exchanged in Type A zeolite particles having a diameter of about 2.5 μ. Another formulation, AJ-10N, consists of about 2% by weight silver ion-exchanged in Type A zeolite particles having a diameter of about 2.5 μ. Another formulation, AW-80, contains 0.6% by weight of silver ion-exchanged in Type A zeolite particles having a diameter of about 1.0 μ. Another formulation, AJ-80N, consists of about 2% by weight silver ion-exchanged in Type A zeolite particles having a diameter of about 1.0 μ. These zeolites preferably contain about between 0.5% and 25.0% by weight of ion-exchanged ammonium.

In a preferred embodiment, the inorganic antimicrobial agent can be of the type designated HealthShield, which is sold by the assignee of the subject application. This material is basically a zeolite, this being a metal having one or the whole of the metal substituted by at least one kind of an ion exchangeable metal selected from the group consisting of Ag, Cu and Zn. A typical particle size for the agent is between 0.8 and 10 microns. The agent is dispersed on the coating material 18 in the quantity of between 0.5 and 20% by weight, more preferably between 0.5 and 10% and most preferably between 0.5 and 5% of the matter that remains on the fabric, exclusive of the fabric. The particles adhere to the coating material while it is wet and become embedded in the coating material 18 as it dries.

In accordance with the invention, other inorganic antimicrobial agents, i.e., those containing silver, copper, lead, gold tin, zinc and mercury. can be used.

As shown in FIG. 4, after the antimicrobial agent 20 is applied to the wet coating material 18, the product is cured, that is, dried, with air under pressure, for example at 60 psi. This removes all of the matter, coating material and antimicrobial agent, in the fabric pores 14. As shown, each of the fabric fibers has on one surface thereof the coating material 18 in which are the embedded particles of the antimicrobial agent 20. If both surfaces of the fabric are treated, the entirety of the fabric would have the same appearance. In any case, the fabric pores 14 would be clear. This maintains fabric pliability.

In another embodiment of making the porous antimicrobial fabric, the inorganic antimicrobial is blended into the textile coating material, such as of the type described above. The mixture is then applied to the base fabric by a spraying process, as previously described, or by dipping. Here also, the fabric is preferably held under tension. This eliminates the step of dusting the fibers with the particles of the agent.

To complete the process for obtaining the porous fabric, in each type of application of the mixture of coating material and antibiotic agent described above, the wet fabric is held under tension and is subjected to a blowing operation to remove matter from the fabric pores. This results in the fabric substantially retaining its porosity. Thus, the fabric will be relatively more flexible than if the pores were not clear.

As explained above, the coating materials can include, for example, acrylic, polyurethane, silicone, latex, polyglycolic lactic acid or other biodegradable polymer, especially one that is a hydrophilic, non- degrading polymer such as a hydrophilic polyurethane, for example TECOPHILIC which is made by Thermedics. Use of antimicrobial agents in hydrophilic materials is also described in an application filed on even date herewith, assigned attorney docket number 1985/OE556 and entitled "Antibiotic Hydrophilic Polymer Coating". The inorganic antimicrobial agent mixed with the coating material is one of the type discussed above and the concentration of the agent in the dry coating material is 0.01 to 50%, preferably 0.1 to 20% and most preferably from 0.5 to 10%.

The resulting fabric, made either by applying the inorganic agent to an adherent coating material, or as part of a mixture with the coating material by spraying or dipping, is a piece of fabric that is antimicrobial, pliable and porous.

A preferred embodiment of the fabric of the invention utilized the following:

| | |
|---|---|
| fiber material: | polyester |
| silicone mixture: | 50% RTV and 50% xylene |
| thickness of silicone layer: | 1–5 microns |
| agent particle size: | 1–2.5 microns |
| agent dispersal factor: | 1% |
| air pressure: | 60 psi |

The antibiotic properties of the antibiotic zeolite particles of the invention may be assayed while in aqueous formulations using conventional assay techniques, including for example determining the minimum growth inhibitory concentration (MIC) with respect to a variety of bacteria, eumycetes and yeast. In such a test, the bacteria listed below may be employed:

*Bacillus cereus* var *mycoides,*
*Escherichia coli,*
*Pseudomonas aeruginosa,*
*Staphylococcus aureus,*
*Streptococcus faecalis,*
*Aspergillus niger,*
*Aureobasiduim pullulans,*
*Chaetomium globosum,*
*Gliocladium virens,*
*Penicillum funiculosum,*
*Candida albicans,*
*Saccharomyces cerevisiae,*

The assay for determining MIC can be carried out by smearing a solution containing bacteria for inoculation onto a plate culture medium to which a test sample of the encapsulated antibiotic zeolite particles is added in a particular concentration, followed by incubation and culturing of the plate. The MIC is defined as a minimum concentration thereof required for inhibiting the growth of each bacteria.

Safety and biocompatibility tests were conducted on the antibiotic zeolites employed in the invention. ISO 10993-1 procedures were employed. The following results were obtained:

| | |
|---|---|
| Cytotoxicity: | Non-Toxic |
| Acute Systemic Toxicity: | Non-Toxic |
| Intracutaneous Toxicity: | Passed |
| Skin Irritation Test: | Non-Irritant |
| Chronic Toxicity: | No Observable Effect |
| In-vitro Hemolysis: | Non-Hemolytic |
| 30-day Muscle Implant Test: | Passed |
| 60-day Muscle Implant Test: | Passed |
| 90-day Muscle Implant Test: | Passed |
| Ames Mutagenicity Test: | Passed |
| Pyrogenicity: | Non-Pyrogenic |

Thus, the antibiotic zeolites are exceptionally suitable under relevant toxicity and biocompatibility standards for use in the fabric.

2. Fabric Fully Coated with Inorganic Antimicrobial Agent

By not using the pressurized drying step described above for blowing the matter from the fabric pores, an antimicrobial fabric is formed that is fully coated. That is, the fabric wetted with the coating material and inorganic agent is permitted to dry at ambient temperature or in a slightly heated environment. With this type of drying, it is not necessary to hold the fabric under tension. The resulting fabric product will be fully coated with the mixture of coating material and embedded antimicrobial agent particles.

In a further embodiment of making the fully coated antimicrobial fabric, the blend of the inorganic antimicrobial and elastomeric coating material is kneaded into the fabric. The kneading takes place without the fabric being held under tension. The blend coats the fabric fibers and fills the pores. The resulting fabric is fully coated with the antimicrobial agent.

3. Fabric with Integral Antimicrobial Agent

In this type of fabric, the fibers are either of a plurality of the mono-filament type, such as of a plurality of polyester filaments, formed in bundles, such as by twisting, or of a naturally multi-filament type, such as cotton. The object is that the fibers themselves have spaces, gaps or voids into which the antimicrobial agent can be placed. For example, a dough or slurry of the antimicrobial agent is kneaded into a fabric of this type and the agent will be embedded in the spaces of the bundle of the plurality of mono-filaments forming a fiber or the fiber of natural material. The fabric can be made porous by holding it under tension and blowing out the agent from the pores, as described above. It can be left non-porous by permitting the agent to dry without attempting to remove the particles from the pores.

To make the graft 70, a piece of the fabric of any of the types described above is cut to size and rolled into a generally tubular shape of the required diameter. The edges of the tube are joined together, such as by stitching with sutures or using an acceptable adhesive. Also, some of the coating materials described above have thermosetting properties which would permit joining of the graft tube edges by heat sealing.

As explained above, where the fabric forming the graft is of the fully coated type, it may be desired to coat it with a tissue compatible material such as collagen. This can be accomplished by coating one side of the fabric, to be the outer surface of the graft, with the collagen either before or after the graft is formed. Both surfaces can be coated wit the collagen. The collagen coating can be accomplished by spraying, painting, etc. Alternatively, the fabric can be dipped in a collagen solution either before of after the graft is formed.

The present invention will hereunder be explained in more detail with reference to the following non-limiting working examples.

EXAMPLE 1

A 1"×1" sample of knitted polyester, available from Bard Vascular Systems Division as knitted polyester style no. 6103, was coated with an antibiotic hydrophilic coating as follows.

A coating solution containing 2.90% by weight of hydrophilic polyurethane available as Tecophilic™ from Thermedics; 96.81% tetrahydrofuran; and 0.29% AW-10N zeolite, available from Shinagawa, Inc., was prepared and mixed with a high shear mixer.

An eye dropper was used to apply the coating solution to the polyester sample. The polyester sample was then sprayed with air to remove excess powder and cure the coating.

EXAMPLE 2

A Dow Shaker Test was performed on the polyester sample prepared in Example 1 (hereafter referred to as Sample A) to determine its inhibitory effect against *S. aureus*. The Dow Shaker Test is based on Dow Corporate Test Method 0923 for testing aerobic bacteria by Dow Chemical. The Dow Shaker Test is described below.

Sample A was sterilized at 121°C. for 15 minutes.

A culture tube containing *S. aureus* was prepared by adding one disk of *S. aureus* to the culture tube. From about 2 to 5 ml of broth was added to the culture tube. Then the culture tube was agitated with a vortex mixer until the disk was completely dissolved in the broth. The bacteria in the culture tube were incubated for at least 3 hours at 35° C. The culture tube was then refrigerated at about 2–8° C. until needed for testing.

A 5 ml sample of bacteria from the culture tube was removed and agitated in a vortex mixer. The absorbance of the sample was measured at 475 nm with a spectrophotometer relative to the absorbance of the aforementioned broth. Broth and/or bacteria from the culture tube were added to the sample until an absorbance of about 0.1 absorbance units was obtained. This corresponded to from about 105 to about 106 colony forming units per milliliter (CFU/ml).

5 ml of suspension was extracted from the sample and added to a flask containing 70 ml of sterile buffer. The resulting solution contained from about $10^4$ to about $10^5$ CFU/ml. The flask was capped and shaken on a wrist action shaker for 1 minute at maximum speed. This is referred to as time "0 hours" below.

The number of colony forming units in 1 ml of the solution was determined at time 0 hours by the following procedure. 1 ml of solution was extracted from the flask and added to a vial containing 9 ml of buffer solution to form a 10:1 dilution. The solution was repeatedly diluted with buffer solution until a plate count of about 30 to about 200 CFU/ml was obtained.

1 ml of the solution from the flask and each dilution were transferred to separate petri dishes. About 15–20 ml molten agar was added to each dish. Each dish was rotated 10 times clockwise and 10 times counter-clockwise to evenly distribute the agar and bacteria. Then, each dish was incubated for 18–24 hours at 35° C. A plate count was performed on the petri dish containing from about 30 to about 200 bacteria colony forming units to determine the number of colony forming units.

Also, at time 0 hours, sample A was added to the flask and shaken with a wrist action shaker for 1 hour. The number of colony forming units in 1 ml of the solution in the flask was determined by the procedure above using 2 petri dishes. If the numbers of colony forming units in the 2 petri dishes were not within 15% of each other, the entire Dow Shaker Test was repeated.

The number of colony forming units in 1 ml of the solution was also determined after shaking the flask with a wrist action shaker for 18 and 24 hours.

A control was tested by the same procedure as sample A. The control was a 1"×1" sample of knitted polyester, available from Bard Vascular Systems Division as knitted polyester style no. 6103.

The number of colony forming units at times 0 hours, 1 hour, 18 hours, and 24 hours for sample A and the control are shown in Table 1. The percentage of bacteria killed by sample A and the control at times 1 hour, 18 hours, and 24 hours are shown in Table 2.

TABLE 1

| Sample | Bacteria Counts of *S. aureus* (Colony Forming Units) | | | |
|---|---|---|---|---|
| | 0 hours | 1 hour | 18 hours | 24 hours |
| Sample A | 780,000 | 2,145,000 | 85,000 | 3,700 |
| Control | 480,000 | 12,400,00 | 4,720,00 | 4,300,000 |

TABLE 2

| Sample | % Killed | | |
|---|---|---|---|
| | 1 hour | 18 hours | 24 hours |
| Sample A | 0 | 89.10% | 99.53% |
| Control | 0 | 0 | 0 |

As indicated in Table 2, Sample A exhibited 99.53% inhibition of *S. aureus* after 24 hours of contact with the bacteria.

We claim:

1. A porous, flexible, medical graft comprising:
   (a) fabric material in a generally tubular shape; and
   (b) ceramic particles bound to the fabric material, the particles comprising antimicrobial metal cations ion-exchanged thereon, wherein some or all of the ceramic particles are exteriorly exposed to permit entry into the particles of water and cations, thereby effecting an ion exchange reaction, which releases antibiotic cations from the ceramic particles in an antimicrobially effective amount.

2. The medical graft of claim 1 wherein the ceramic particles are bound to the graft by a polymeric coating material.

3. The medical graft of claim 1 wherein the ceramic particles comprise zeolite particles dispersed on the coating material and wherein the zeolite constitutes between 0.5 and 20% of the weight of the graft, exclusive of the fabric.

4. The graft of claim 2 wherein the coating material comprises an elastomeric material selected from the group consisting of acrylic, polyurethane, silicone, latex, polyglycolic lactic acid, a biodegradable polymer, a hydrophilic biodegradable polymer, and a non-degrading polymer.

5. The graft of claim 2 wherein the coating material comprises a hydrophilic polyurethane.

6. The graft of claim 1 wherein said ceramic particles comprise zeolite particles.

7. The graft of claim 4 wherein the ceramic particles have a size between 0.8 and 10 microns.

8. The graft of claim 1 wherein the fibers of the fabric comprise a polymer selected from the group consisting of cotton, nylon, polyester, PTFE, e-PTFE and blends of these materials.

9. The graft of claim 1 further comprising a coating of a tissue compatible material on at least an exterior surface of the graft.

10. A method of making a medical graft comprising:
   (a) providing porous fabric treated with ceramic particles bound to the fabric material, the particles comprising antimicrobial metal cations ion-exchanged thereon, wherein the process results in some or all of the ceramic particles being exteriorly exposed to permit entry of water and cations into the ceramic particles, thereby effecting an ion exchange reaction, which releases antibiotic cations from the ceramic particles in an antimicrobially effective amount; and (b) forming said fabric piece into a generally tubular shape to form said graft with said antibiotic agent.

11. The method of claim 10 further comprising the step of coating at least the outer surface of said graft with a tissue compatible material.

12. The method of claim 10 wherein step (a) comprises applying a coating material containing said antimicrobial agent to cover the fabric piece and removing matter from the fabric pores.

13. The method of claim 12 wherein said applying step comprises first applying a wet coating material to the fabric and then applying the ceramic particles in powdered form to the wet coating material.

14. The method of claim 12 wherein said applying step comprises applying a mixture of the coating material and the ceramic particles to said fabric.

15. The method of claim 12 wherein said removing step comprises applying a gas under pressure to said fabric.

16. The method of claim 12 wherein said fabric is held under tension during the application of said coating material.

17. The method of claim 13 wherein said fabric piece is held under tension during application of said coating material and removing of said matter in said fabric pores.

18. A method of producing a porous, pliable antimicrobial fabric comprising:
(a) providing a porous fabric; and
(b) applying to said fabric ceramic particles while leaving pores of said fabric open, wherein:
(i) the ceramic particles bound to the fabric comprise antimicrobial metal cations ion-exchanged thereon; and
(ii) some or all of the ceramic particles are exteriorly exposed to permit entry of water and cations into the ceramic particles, thereby effecting an ion exchange reaction, which releases antibiotic cations from the ceramic particles in an antibiotically effective amount.

19. The method of claim 18 wherein said applying step comprises applying a coating material and the ceramic particles to cover the fabric piece and removing matter from the fabric pores.

20. The method of claim 19 wherein said applying step comprises first applying a wet coating material to the fabric and then applying the ceramic particles in powdered form to the wet coating material.

21. The method of claim 19 wherein said applying step comprises applying a mixture of the coating material and the ceramic particles to the fabric.

22. The method of claim 19 wherein the removing step comprises applying a gas under pressure to the fabric.

23. The method of claim 19 wherein the fabric is held under tension during the application of the coating material.

24. The method of claim 19 wherein the fabric piece is held under tension during application of the coating material and during removing of the matter from said fabric pores.

25. The method of claim 19 wherein fibers of the fabric are of a type having voids, and the step of applying comprises placing said antimicrobial agent into said voids.

26. A pliable antimicrobial fabric comprising a porous fabric comprising an antimicrobial metal ion-generating inorganic antimicrobial agent on fibers of the fabric, with the pores of the fabric left open.

27. The fabric of claim 26 wherein said antimicrobial agent is in a coating on the fibers of said fabric piece.

28. A porous, flexible medical graft comprising fabric material formed in a generally tubular shape, wherein at least a portion of the fabric material is coated with a polymeric coating material incorporating inorganic ceramic particles, such that some or all of the ceramic particles are exteriorly exposed to release antibiotic metal cations in an antimicrobially effective amount when the medical graft is implanted in vivo.

29. A non-porous medical graft, the graft comprising fabric material formed in a generally tubular shape, wherein:
(a) the fabric material comprises a first coating comprising a polymeric coating material incorporating inorganic ceramic particles; and
(b) the fabric comprises a second coating comprising a tissue growth-promoting material;

such that some or all of the ceramic particles are exteriorly exposed to release antibiotic metal cations in an antimicrobially effective amount when the medical graft is implanted in vivo.

* * * * *